United States Patent
Hatib et al.

(10) Patent No.: US 8,491,487 B2
(45) Date of Patent: Jul. 23, 2013

(54) DETECTION OF PARAMETERS IN CARDIAC OUTPUT RELATED WAVEFORMS

(75) Inventors: Feras Hatib, Irvine, CA (US); Luchy Roteliuk, Lake Forest, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 427 days.

(21) Appl. No.: 12/699,540

(22) Filed: Feb. 3, 2010

(65) Prior Publication Data
US 2010/0204592 A1 Aug. 12, 2010

Related U.S. Application Data

(60) Provisional application No. 61/151,670, filed on Feb. 11, 2009.

(51) Int. Cl.
*A61B 5/0245* (2006.01)
(52) U.S. Cl.
USPC ............ 600/526; 600/509; 600/513; 600/519
(58) Field of Classification Search
USPC .................................. 600/509, 513, 519, 526
See application file for complete search history.

(56) References Cited

U.S. PATENT DOCUMENTS

| 2002/0022785 A1 | 2/2002 | Romano |
| 2003/0023173 A1 | 1/2003 | Bratteli et al. |
| 2003/0036685 A1 | 2/2003 | Goodman |
| 2004/0097814 A1 | 5/2004 | Navakatikyan et al. |

OTHER PUBLICATIONS

International Search Report, Sep. 27, 2010.

*Primary Examiner* — Joseph Dietrich
(74) *Attorney, Agent, or Firm* — Michael Crapenhoft

(57) ABSTRACT

Methods for detecting parameters in cardiac output related waveforms are described. The methods include methods for detecting individual heart beat cycles in a cardiac output related waveform, methods for detecting an error in an assigned starting point for an individual heart beat cycle in a cardiac output related waveform, methods for detecting a dichrotic notch for an individual heart beat cycle in a cardiac output related waveform, and methods for detecting an error in an assigned dichrotic notch for an individual heart beat cycle in a cardiac output related waveform. The identification of these parameters is important for a clinician as these parameters form the basis for the calculation of many other cardiac output related parameters.

7 Claims, 11 Drawing Sheets

DETECTION OF PARAMETERS IN CARDIAC OUTPUT RELATED WAVEFORMS

CLAIM OF PRIORITY UNDER 35 U.S.C. §119

The application claims the benefit of U.S. Provisional Application No. 61/151,670, filed Feb. 11, 2009, entitled "Detection of Parameters in Cardiac Output Related Waveforms" and assigned to the assignee hereof and hereby incorporated by reference in its entirety.

BACKGROUND

Many of the parameters that can be determined from cardiac output related waveforms, e.g., peripheral pressure waveforms, are important not only for diagnosis of disease, but also for "real-time," i.e., continual, monitoring of clinically significant changes in a subject. Various methods exist to identify and/or calculate these parameters based on analysis of various features in cardiac output related waveforms. Few hospitals are without equipment that employ these methods to monitor one or more cardiac output related parameters in an effort to provide a warning that a subject's condition is changing.

SUMMARY

Methods for detecting parameters in cardiac output related waveforms are described. The methods include methods for detecting individual heart beat cycles in a cardiac output related waveform, methods for detecting an error in an assigned starting point for an individual heart beat cycle in a cardiac output related waveform, methods for detecting a dichrotic notch for an individual heart beat cycle in a cardiac output related waveform, and methods for detecting an error in an assigned dichrotic notch for an individual heart beat cycle in a cardiac output related waveform.

The methods for detecting individual heart beat cycles in a cardiac output related waveform include providing cardiac output related waveform data and calculating a first derivative function for the waveform data. The order of the data for the first derivative function is then reversed in time. Next the amplitude of the first derivative function is compared to a threshold value, with the threshold value being a percentage of the maximum amplitude in the first derivative function. The start of a heart beat cycle is then determined by identifying the first time the first derivative function equals zero immediately after the point (i.e., prior in time) at which the amplitude of the first derivative function is greater than the threshold value in the reversed time order data. The first time the first derivative function equals zero indicates the beginning of a heart beat cycle.

The methods for detecting an error in an assigned staring point for an individual heart beat cycle in a cardiac output related waveform include providing cardiac output related waveform data for an individual heart beat cycle, the individual heart beat cycle having a predetermined starting point, and determining a maximum value of the cardiac output related waveform data. Next a first point in the cardiac output related waveform is determined, the first point being the first point on the cardiac output related waveform prior to the maximum value that has a value equal to one-half the maximum value. The portion of the heart beat cycle between the starting point and the first point is then searched for a local maximum. If a local maximum is found, the portion of the heart beat cycle between the first point and the local maximum is searched for a local minimum point, and the starting point for the individual heart beat is reassigned to the local minimum point.

The methods for detecting a dichrotic notch for an individual heart beat cycle in a cardiac output related waveform include providing cardiac output related waveform data for an individual heart beat cycle, the individual heart beat cycle having a previously determined starting time point, and calculating a first derivative function for the waveform data. Next a first time point and a second time point are determined from the first derivative function, the first time point being the first zero crossing after the starting time point for the first derivative function and the second time point being the second zero crossing after the starting time point for the first derivative function. A second derivative function is also calculated for the waveform data and a third time point and a fourth time point are determined from the second derivative function, the third time point being the first zero crossing after the second time point for the second derivative function and the fourth time point being the second zero crossing after the second time point for the second derivative function. Then the portion of the second derivative function between the third time point and the fourth time point is searched for a local maximum, the local maximum occurring at a fifth time point. The fifth time point corresponds to the time point at which the dichrotic notch is located in the cardiac output related waveform data for the individual heart beat cycle.

The methods for detecting an error in an assigned dichrotic notch for an individual heart beat cycle in a cardiac output related waveform include providing cardiac output related waveform data for an individual heart beat cycle, the individual heart beat cycle having a previously determined dichrotic notch time point, a previously determined starting time point, a previously determined cardiac output maximum point, and a previously determined ending time point, and calculating a first derivative function for the waveform data. Then all the local maximums between the cardiac output maximum point and a search time point in the first derivative function are determined, the search time point being starting time point plus two-thirds the time between the starting time point and the ending time point. If more than one local maximum is found, the dichrotic notch is assigned to the time point at the second local maximum.

DETAILED DESCRIPTION

Methods for detecting parameters in cardiac output related waveforms are described. Specifically, the methods described herein include detecting individual heart beat cycles in a cardiac output related waveform, detecting an error in an assigned starting point for an individual heart beat cycle in a cardiac output related waveform, detecting a dichrotic notch for an individual heart beat cycle in a cardiac output related waveform, and detecting an error in an assigned dichrotic notch for an individual heart beat cycle in a cardiac output related waveform. The individual heart beat cycles and the dichrotic notch in a cardiac output related waveform, in addition to themselves being important parameters for a clinician, form the basis for the calculation of many other cardiac output related parameters, thus, the initial accurate identification of heart beat cycles and dichrotic notch forms the basis for a clinician to appropriately provide treatment to a subject.

As used herein, the phrase cardiac output related waveform is used to indicate a signal related to, e.g., proportional to, derived from, or a function of, cardiac output. Examples of such signals include, but are not limited to, peripheral arterial and central aortic pressure and/or flow, pulse oxymetry waveforms, impedance plethysmography waveforms, and Doppler waveforms. The term peripheral arterial pressure is intended to mean pressure measured at any point in the arterial tree, e.g., radial, femoral, or brachial, either invasively or non-invasively. If invasive instruments are used, in particular, catheter-mounted pressure transducers, then any artery is a possible measurement point. Placement of non-invasive transducers will typically be dictated by the instruments themselves, e.g., finger cuffs, upper arm pressure cuffs, and earlobe clamps. Peripheral arterial pressure increases the further away from the heart the measurement is taken. Regardless of the specific instrument or measurement used, the data obtained will ultimately yield an electric signal corresponding (for example, proportional) to cardiac output.

Figure 1:
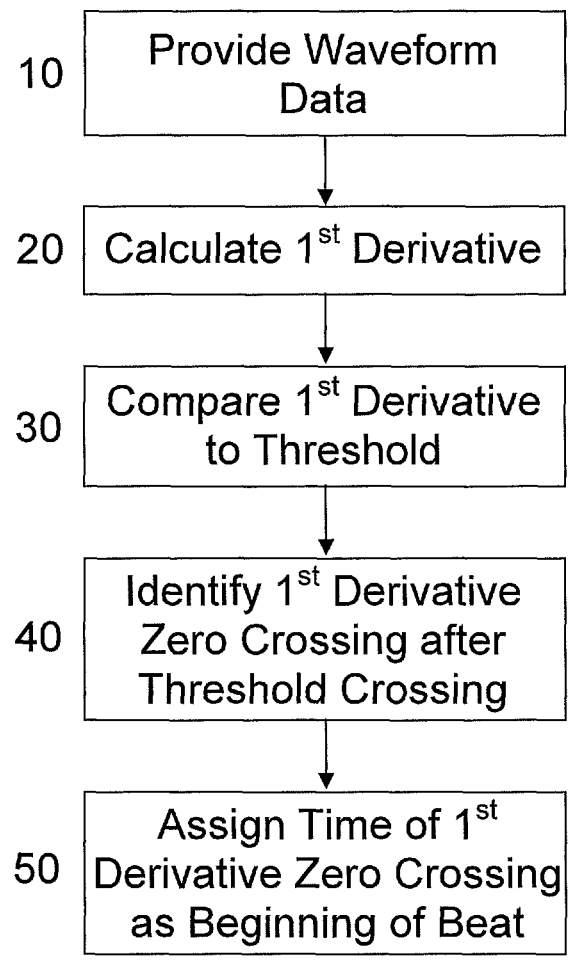
FIG. 1 shows a flow chart illustrating an example of logic for detecting individual heart beat cycles in cardiac output related waveforms.

The method for detecting individual heart beat cycles in cardiac output related waveforms as disclosed herein is shown as a flow chart in FIG. 1 and involves providing cardiac output related waveform data (10), and calculating a first derivative function for the waveform data and reversing the time order of the data (20). The amplitude of the first derivative function is compared to a threshold value (30), i.e., a percentage of the maximum amplitude in the first derivative function. The start of a heart beat cycle is determined by identifying the first time the first derivative function equals zero immediately after the point at which the amplitude of the first derivative function is greater than the threshold value in the reversed time order data (40), i.e., the first time the first derivative function equals zero indicates the beginning of a heart beat cycle (50).

Figure 2:
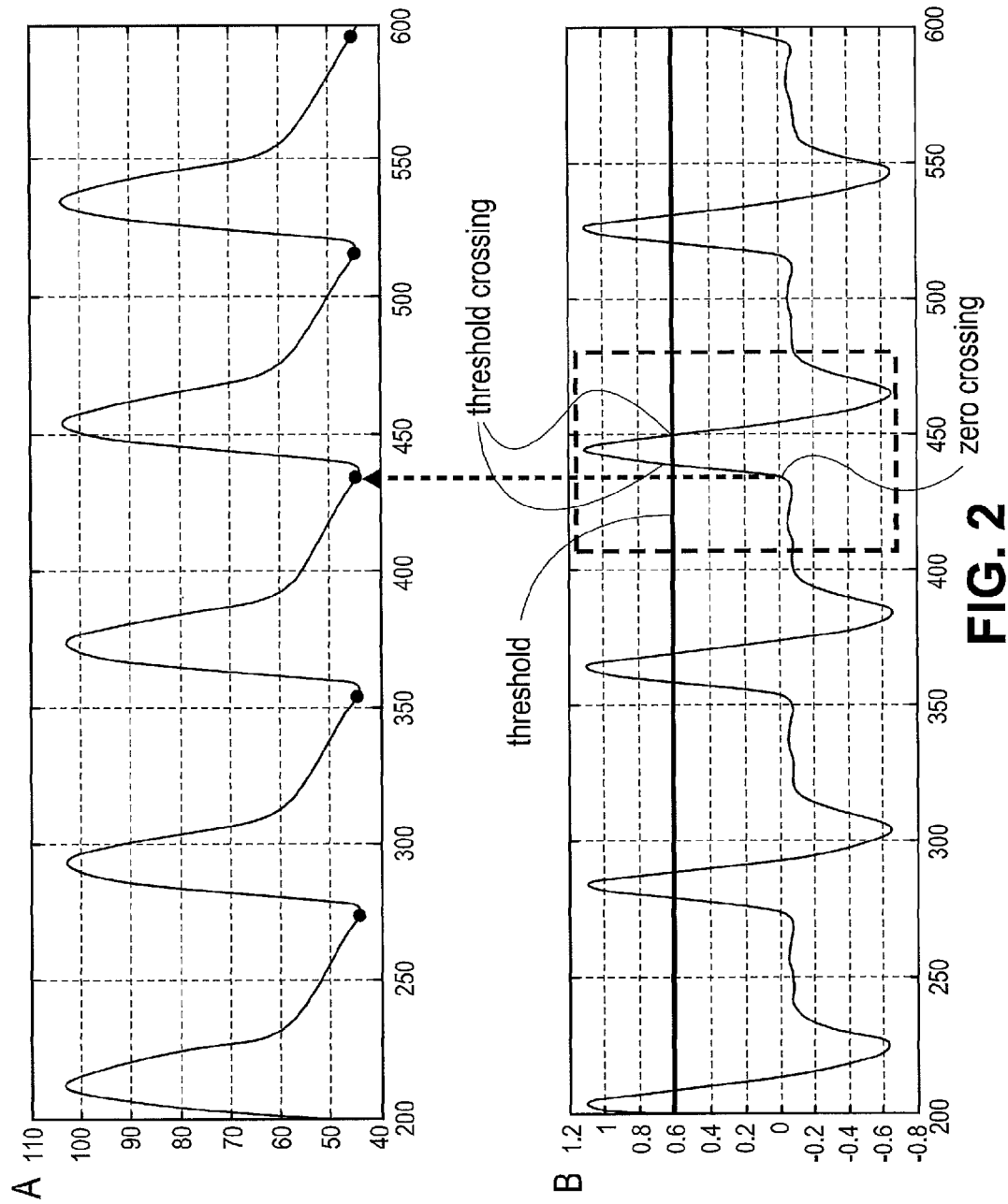
FIG. 2A shows an arterial pressure waveform taken over several heart beat cycles.
FIG. 2B shows the first derivative function of the arterial pressure waveform shown in FIG. 2A.

FIG. 2A is an example of an arterial pressure waveform taken over several heart beat cycles. The individual heart beat cycles are indicated by dots near the waveform minimum values. Applying the method for detecting individual heart beat cycles just described involves calculating the first derivative function, which for the waveform shown in FIG. 2A is shown in FIG. 2B (note the first derivative function is not shown in FIG. 2B as reversed in time order). Next the first derivative function is compared to a threshold value, which is shown in FIG. 2B for the purpose of this example as a thick line. Next, the first zero crossing immediately after (shown as prior in time to) the point at which the amplitude of the first derivative function is greater than the threshold value is located. The first zero crossing for the portion of the first derivative function indicated by a dashed line is noted in FIG. 2B. For a derivative function as shown in FIG. 2B, the choice of a threshold crossing on the rising or descending portion of the first derivative function peak does not impact the identification of the first zero crossing prior to the peak. The identified zero crossing time is the time at which the individual heart beat cycle began (see dashed arrow pointing from FIG. 2B to FIG. 2A). To calculate the next heart beat cycle, the first derivative function is searched for the next point at which the amplitude of the first derivative function is greater than the threshold value and the process is repeated. The method can be repeated until the end of the provided waveform is reached (or indefinitely if data is continuously provided, e.g., in real-time monitoring).

The waveform data can be filtered to remove high and low frequency noise prior to taking the calculating the first derivative waveform. A high-pass filter, for example, can be used to suppress baseline drift and to eliminate the effect of respiration in the subject. A high-pass filter useful with the methods described herein could achieve zero-phase distortion by using forward and reverse digital filtering techniques to retain the same phase as the input signal. Anther parameter for a high-pass filter useful with the methods described herein includes a low frequency (e.g., 0.25 Hz) cut-off frequency to remove baseline drift and respiration. For further example, a low-pass filter can be used to smooth the waveform signal prior to calculating the first derivative. A low-pass filter can reduce the effect of any rapid time-domain transitions and/or variations in the arterial pulse pressure signal. A finite impulse response filter can be used to limit time delay in the low-pass filtering operation. The use of low- and high-pass filters to aid in the processability of data is well known to those of skill in the art.

A common problem in detecting the cardiac beat cycles in cardiac output-related waveforms is heart rate irregularities. Examples of such heart rate irregularities include, but are not limited to, the occurrence of premature atrial or ventricular contractions, arrhythmia, and atrial fibrillation. Heart rate irregularities typically include premature beats, which could occur at any time. These premature beats typically generate less volume and lower pressure than the main beats. The lower volume and pressure of these beats causes the appearance of small beats in the signal of all cardiac output related waveforms. The small beats generated by the premature cardiac contractions have very similar amplitude and frequency characteristics as the pressure reflections that could occur during the diastolic phase or during the late systolic phase of the cardiac output related waveform making these beats hard to differentiate from pressure reflections. For example, if lower thresholds are used to detect the small beats generated by premature cardiac contractions, large pressure reflections could be erroneously counted as cardiac cycles.

Figure 3:
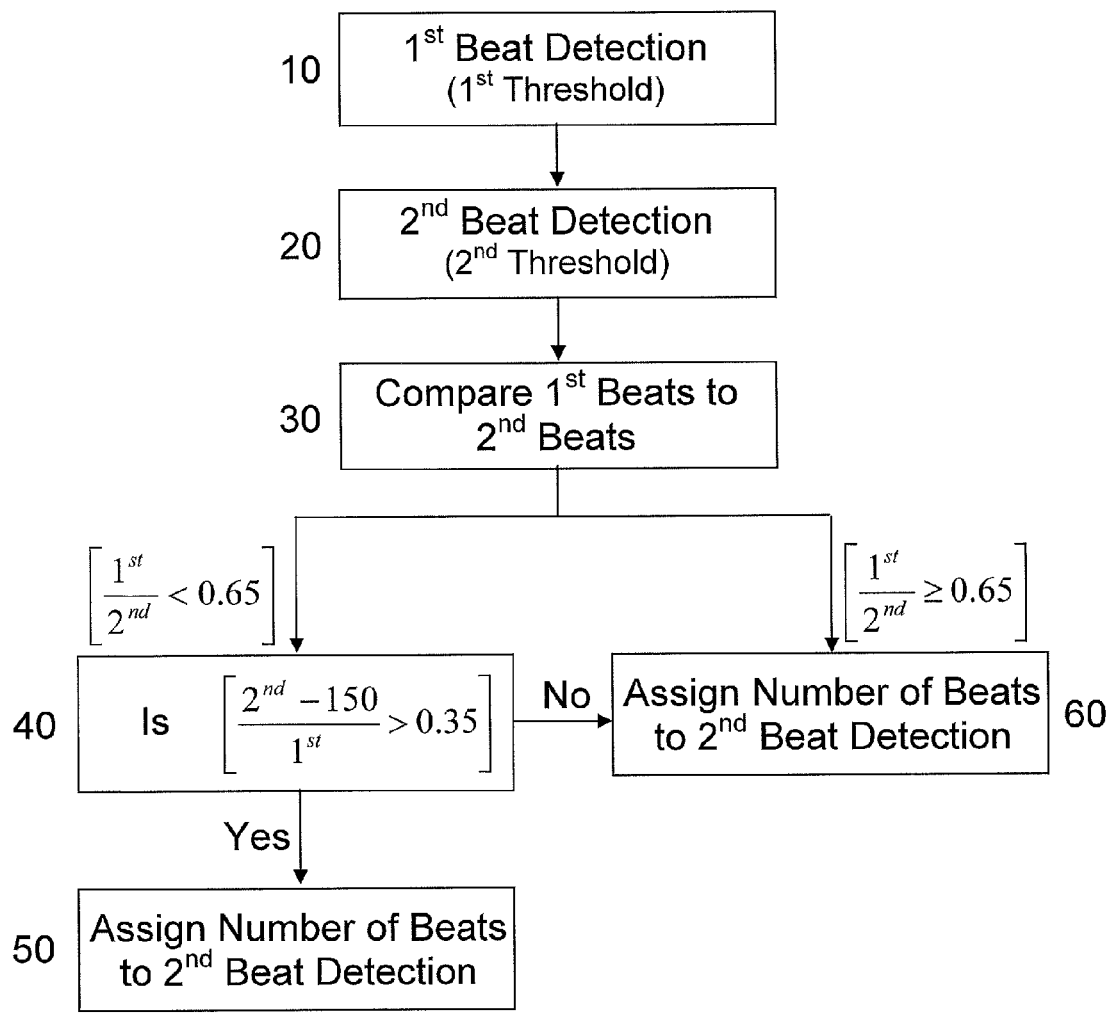
FIG. 3 shows a flow chart illustrating an example of logic for verifying the number of individual heart beat cycles in cardiac output related waveforms.
Figure 4:
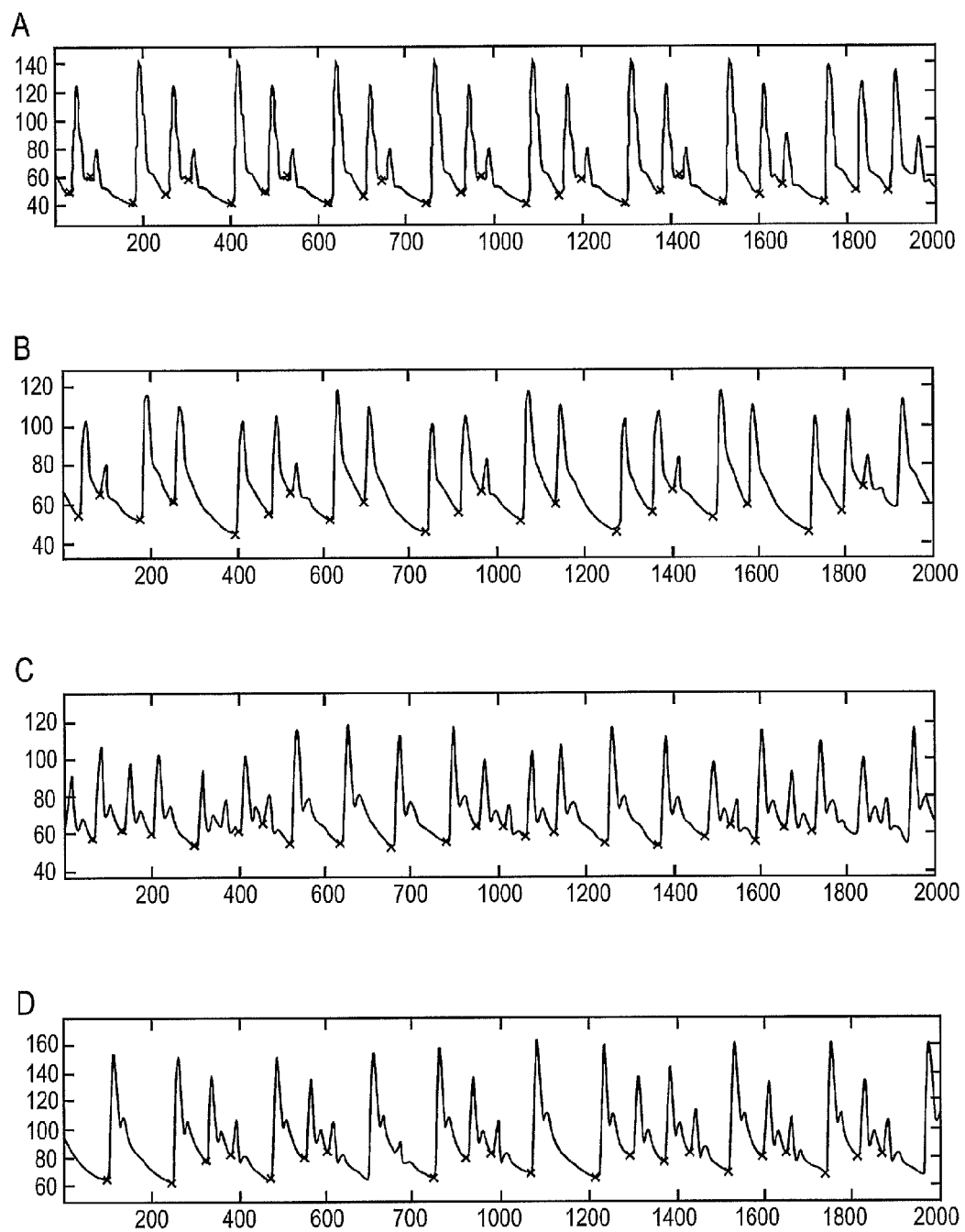
FIGS. 4A-D show examples of cardiac output waveforms in which arrhythmia is occurring.

To overcome the potential for counting pressure reflections as cardiac cycles, the method for detecting individual heart beat cycles in cardiac output related waveforms as described above can be repeated at different threshold levels to verify the number of heart beat cycles detected. To verify the number of heart beat cycles (as shown in FIG. 3), the method is performed as described above using a first threshold (10), then performed a second time using a second (lower) threshold value (20). Next, the number of heart beats detected using the different threshold values is compared (30). If the ratio of the number of heart beat cycles using the first threshold value to the number of heart beat cycles using the second threshold value is less than 65%, but the number of beats per minute above 150 is not greater than 35% of the beats per minute detected then using the heart beat cycles determined using the second threshold value as the actual number of heart beat cycles (40). If the ratio of the number of heart beat cycles using the threshold value to the number of heart beat cycles using the second threshold value is less than 65% and the number of beats per minute above 150 is greater than 35% of the beats per minute detected then using the heart beat cycles determined using the first threshold value as the actual number of heart beat cycles (50). If the ratio of the number of heart beat cycles using the first threshold value to the number of heart beat cycles using the second threshold value is not less than 65%, then using the heart beat cycles determined using the second threshold value as the actual number of heart beat cycles (60). The method can be repeated using additional pairs of first threshold and second (lower) threshold values.

The choice of a threshold value for use in the method to detect individual heart beat cycles depends upon a variety of factors. Examples of threshold values useful with the methods described herein include 0.8, 0.75, 0.7, 0.65, 0.6, 0.55, 0.5, 0.45, 0.4, 0.35 and 0.3. Examples of pairs of threshold and lower threshold values useful with these methods include various combinations of these threshold values, such as, 0.75 and 0.6 or 0.6 and 0.3. Other threshold values and pairs of threshold values can be useful depending on the circumstances. FIGS. 4A-4D show examples of cardiac output waveforms in which arrhythmia is occurring. Each of these waveforms represent very challenging situations of beat detection from cardiac output related waveforms. The present method was used to successfully detect the beats shown with the dots. FIGS. 4A-4D demonstrate the excellent performance of this method in very challenging conditions.

Figure 5:
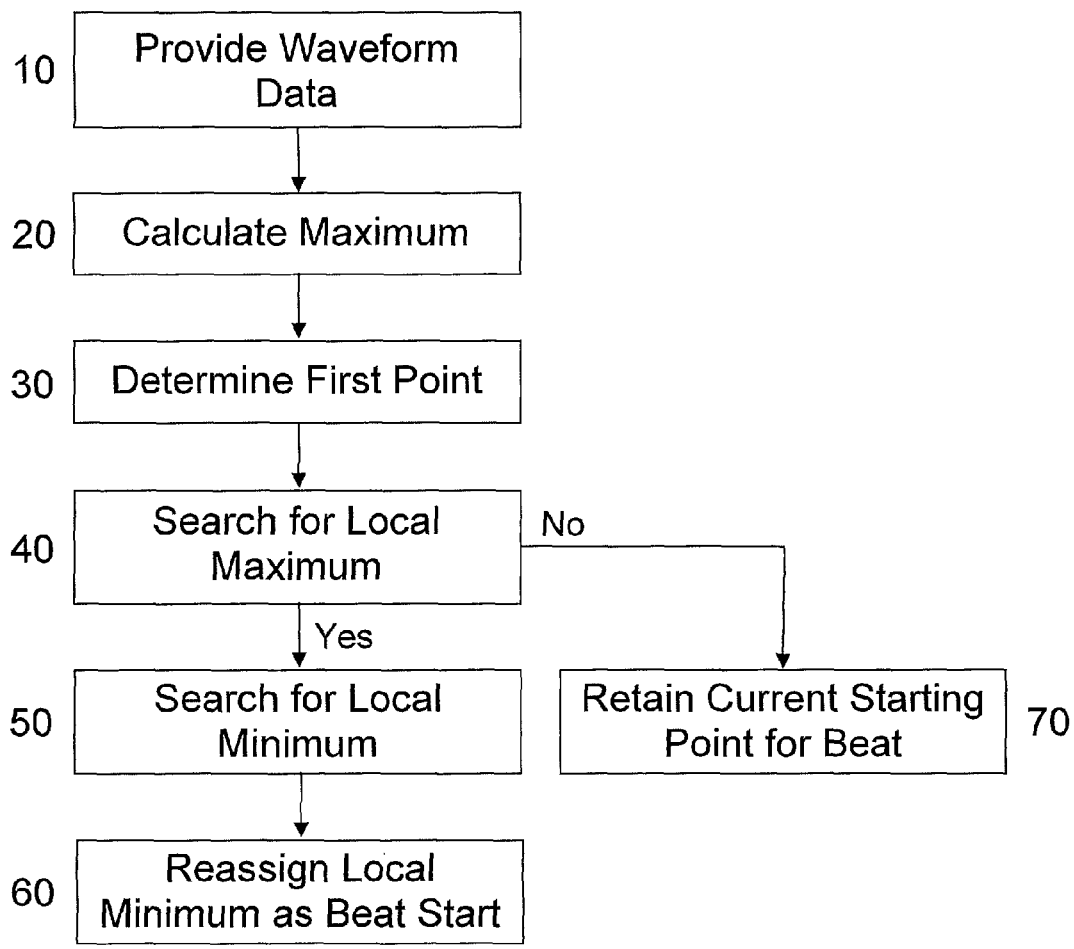
FIG. 5 shows a flow chart illustrating an example of logic for detecting an error in an assigned staring point for an individual heart beat cycle in a cardiac output related waveform.

Also described herein (and shown as flow chart in FIG. 5) is a method for detecting an error in an assigned staring point for an individual heart beat cycle in a cardiac output related waveform. Examples of situations in which an assigned starting point may be incorrectly assigned include arrhythmia conditions or tachycardia conditions, in which large pressure reflections occur during the diastolic phase of the waveform and the next cardiac cycle starts before the end of the reflection of the diastolic phase of the previous cardiac cycle. In these cases the beginning of a heart beat cycle contains a small peak like that shown in FIGS. 6A and 6B. In these types of situations, standard beat detection methods can erroneously detect the beginning of the beat before the small peak at the minimum point of the diastolic phase of the previous cycle rather than after the peak, where the true start of the beat is located. Such an incorrect detection of the beginning of a beat could cause significant errors in the determination of other cardiac parameters based on the waveform being analyzed. The method for detecting an error in an assigned starting point for an individual heart beat cycle (as shown in FIG. 5) includes providing cardiac output related waveform data for an individual heart beat cycle with a predetermined starting point (10). Next a maximum value of the cardiac output related waveform data is determined (20) and a first point is found (30). The first point being the first point on the cardiac output related waveform prior to the maximum value that has a value equal to one-half the maximum value. Then the portion of the heart beat cycle between the starting point and the first point is searched for a local maximum (40). If a local maximum is found between the starting point and the first point, the portion of the heart beat cycle between the first point and the local maximum is searched for a local minimum point (50), and the starting point for the individual heart beat is reassigned as the local minimum point (60). If a local maximum is not found between the starting point and the first point, the current starting point for the beat is retained (70). The method may further include finding the starting point of the next individual heart beat, which will also be the ending point for the current individual heart beat cycle.

Figure 6:
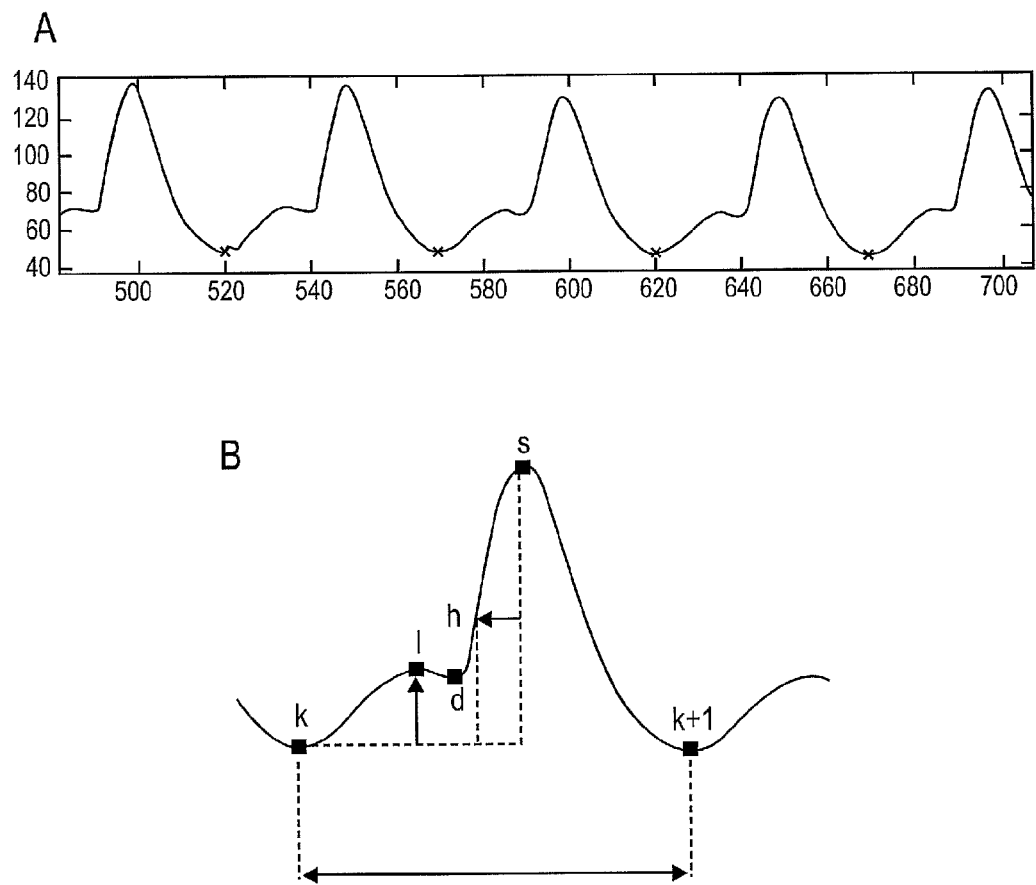
FIG. 6A shows an arterial pressure waveform taken over several heart beat cycles in which the initiation of heart beat cycles have been incorrectly identified.
FIG. 6B shows the relevant points of a heart beat cycle for the application of methods for detecting an error in an assigned staring point for an individual heart beat cycle in a cardiac output related waveform.

To further illustrate this method, FIG. 6A shows a waveform in which the beginning of each heart beat cycle has been incorrectly detected (see the dots at the local minimums). FIG. 6B shows the relevant points of a heart beat cycle for the application of this method, i.e., k is the predetermined starting point for the heart beat cycle (k+1 is the beginning of the next heart beat cycle), s is the maximum value of the cardiac output related waveform data, h is the first point on the cardiac output related waveform prior to the maximum value that has a value equal to one-half the maximum value, l is the local maximum between the starting point and the first point, and d is the correct start of the heart beat cycle as calculated using the method.

Figure 7:
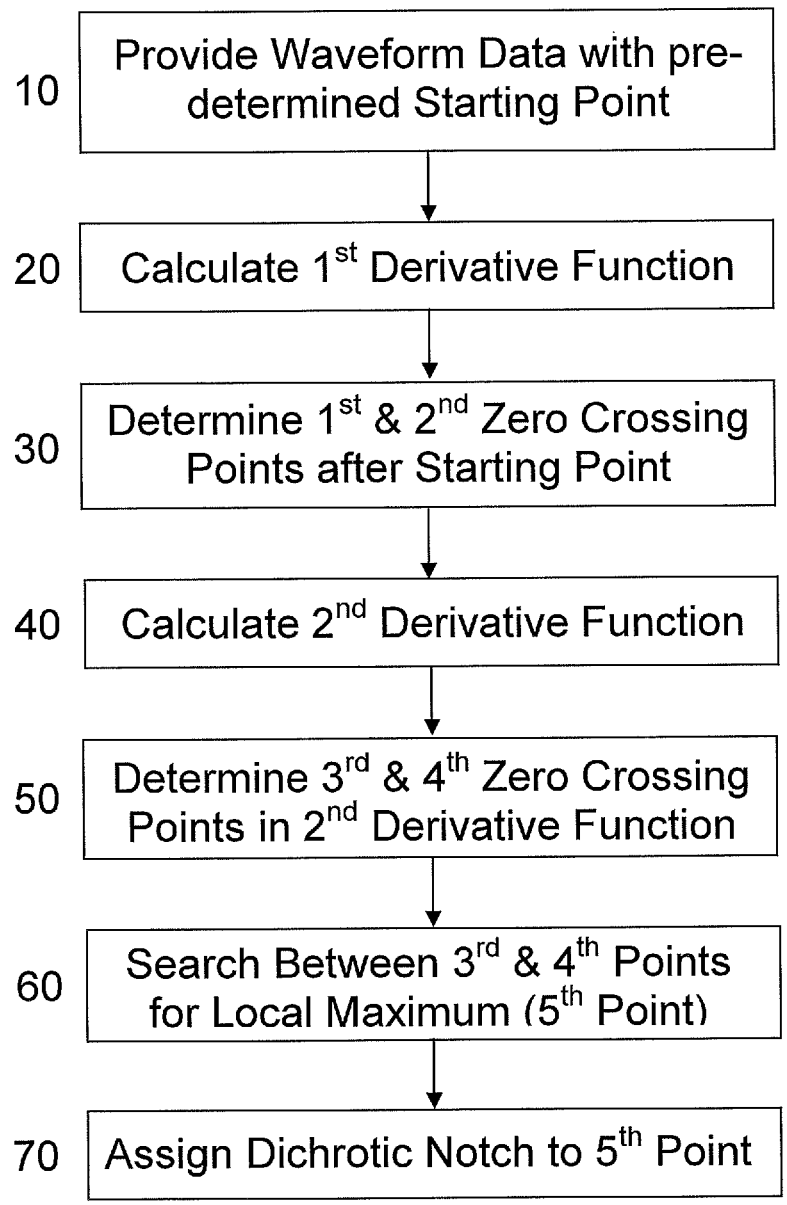
FIG. 7 shows a flow chart illustrating an example of logic for detecting a dichrotic notch for an individual heart beat cycle in a cardiac output related waveform.

Further described herein (and shown in a flow chart in FIG. 7) is a method for detecting a dichrotic notch for an individual heart beat cycle in a cardiac output related waveform. This method includes providing cardiac output related waveform data for an individual heart beat cycle with a previously determined starting point (10) and calculating a first derivative function for the waveform data (20). Next a first time point (the first zero crossing after the starting time point for the first derivative function) and a second time point (the second zero crossing after the starting time point for the first derivative function) are determined from the first derivative function (30). A second derivative function is also calculated for the waveform data (40). Then a third time point (the first zero crossing after the second time point for the second derivative function) and a fourth time point (the second zero crossing after the second time point for the second derivative function) are determined from the second derivative function (50). Next the portion of the second derivative function between the third time point and the fourth time point is searched for a local maximum, the local maximum occurring at a fifth time point (60). Finally, the fifth time point is assigned to be the dichrotic notch. The functions used in this method can be filtered as described above.

Figure 8:
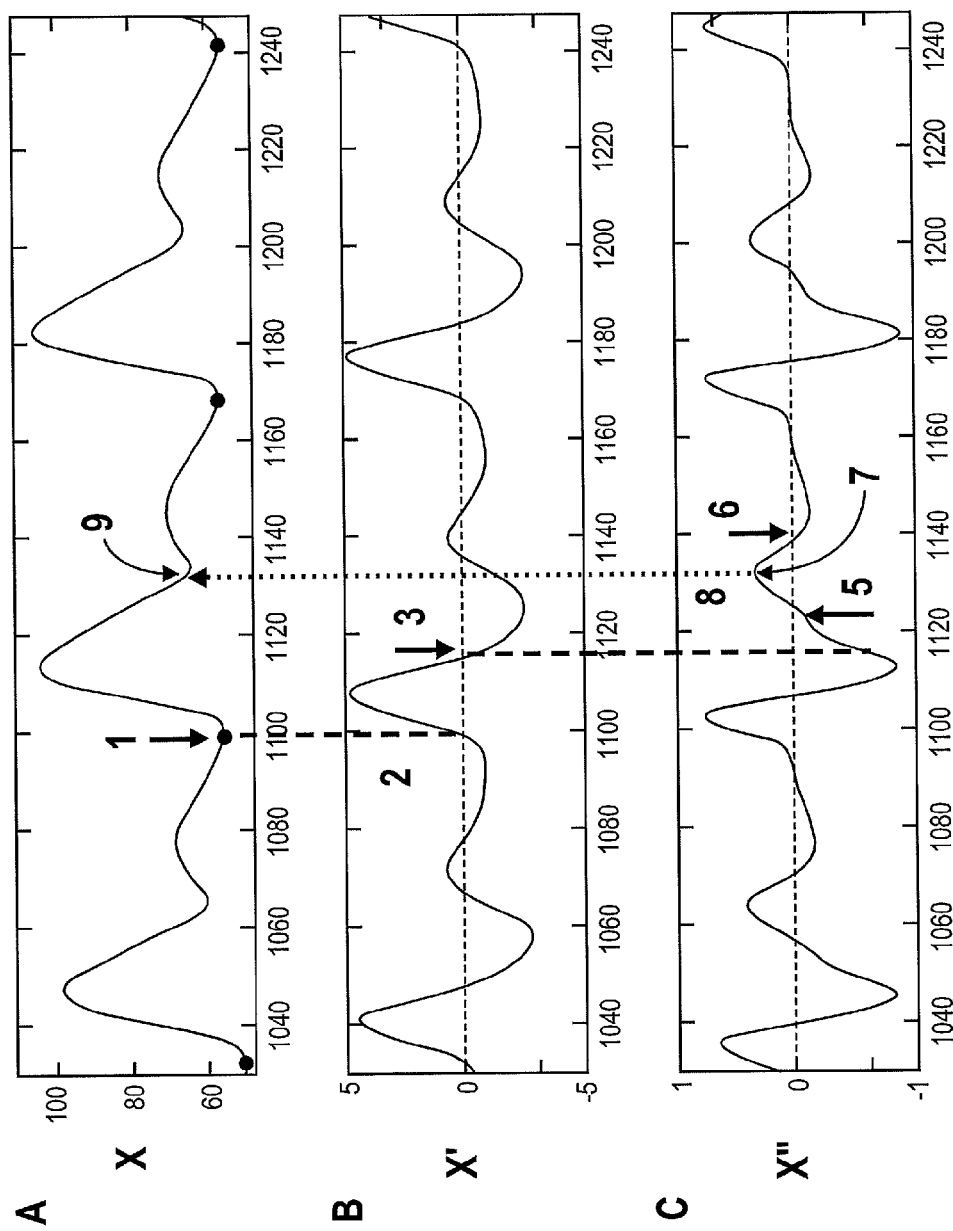
FIG. 8A shows an arterial pressure waveform taken over several heart beat cycles.
FIG. 8B shows the first derivative function of the waveform from FIG. 8A.
FIG. 8C shows the second derivative function of the waveform from FIG. 8A.

To further illustrate this method, FIG. 8 shows cardiac output data analyzed using this method. Specifically, FIG. 8A shows a waveform with three indicated heart beat cycles (dots at local minima), FIG. 8B shows the first derivative function of the waveform shown in FIG. 8A, and FIG. 8C shows the second derivative function of the waveform shown in FIG. 8A. Point 1 of FIG. 8A is the start of the heart beat cycle being analyzed and dashed line 2 between FIGS. 8A and 8B shows the starting time point for the heart beat cycle in the first derivative function and also occurs just prior to the first time point (i.e., the first zero crossing after the starting point) in the first derivative function. Point 3 in FIG. 8B shows the second time point in the first derivative function (i.e., the second zero crossing after the starting time point). Dashed line 4 shows where the second time point is transferred to the second derivative function shown in FIG. 8C to start the search for the third time point (i.e., the first zero crossing after the second time point in the second derivative function) and point 5 in FIG. 8C is the third time point. Point 6 in FIG. 8C is the fourth time point (i.e., the second zero crossing after the second time point in the second derivative function). Point 7 in FIG. 8C (i.e., the fifth time point) is the local maximum between the third time point and the second time point. The time of the fifth point is shown to be transferred back to the waveform of FIG. 8A where the time point indicates the position of the dichrotic notch (shown at point 9).

Figure 9:
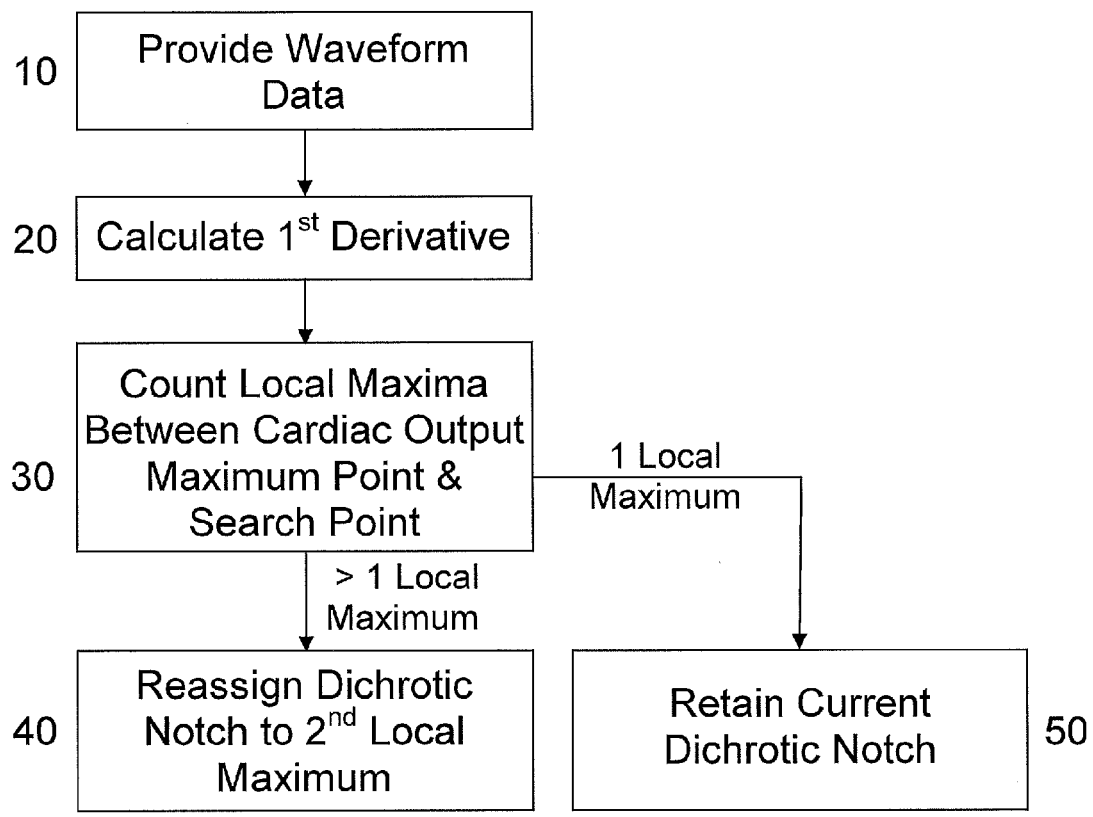
FIG. 9 shows a flow chart illustrating an example of logic for detecting an error in an assigned dichrotic notch for an individual heart beat cycle in a cardiac output related waveform.

Additionally described herein (and shown in a flow chart in FIG. 9) is a method for detecting an error in an assigned dichrotic notch for an individual heart beat cycle in a cardiac output related waveform. These types of errors commonly occur in dichrotic notch detection when large reflected waves are present in the signal around the dichrotic notch location. This method includes providing cardiac output related waveform data for an individual heart beat cycle with a previously determined dichrotic notch time point, a previously determined starting time point, a previously determined cardiac output maximum, and a previously determined end time point (10), and calculating a first derivative function for the waveform data (20). Next, all the local maximums between the cardiac output maximum point and a search time point in the first derivative function are determined (30). The search time point is determined by adding the starting time point and two-thirds of the time interval between the starting time point and the ending time point. If more than one local maximum is found, the dichrotic notch is reassigned to the time point at the second local maximum (40). If only one local maximum is found, the dichrotic notch remains the previously determined dichrotic notch (50).

Figure 10:
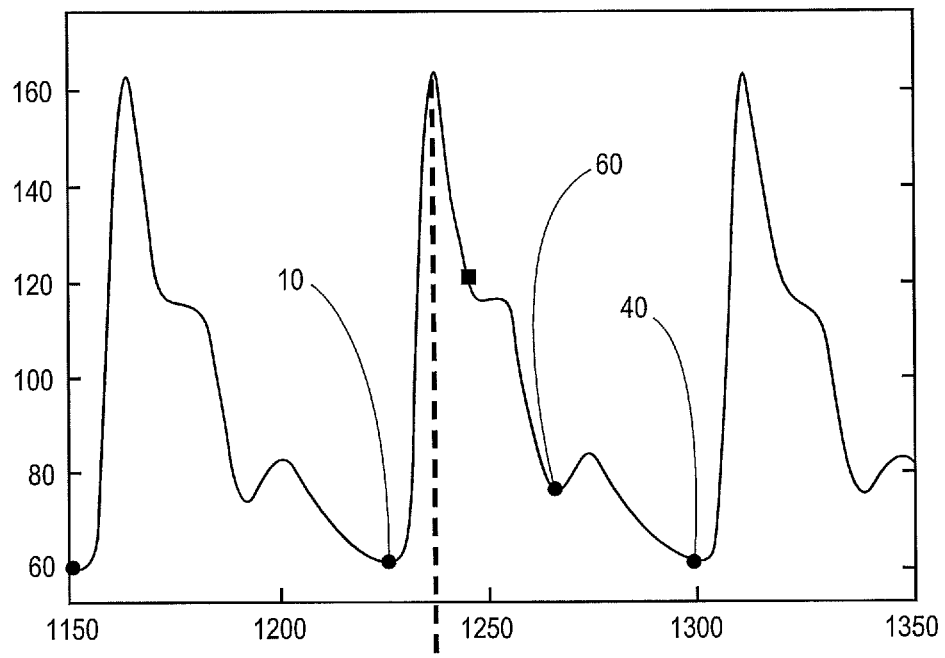
FIG. 10A shows an arterial pressure waveform taken over several heart beat cycles.
FIG. 10B shows the first derivative function of the waveform from FIG. 10A.
Figure 10:
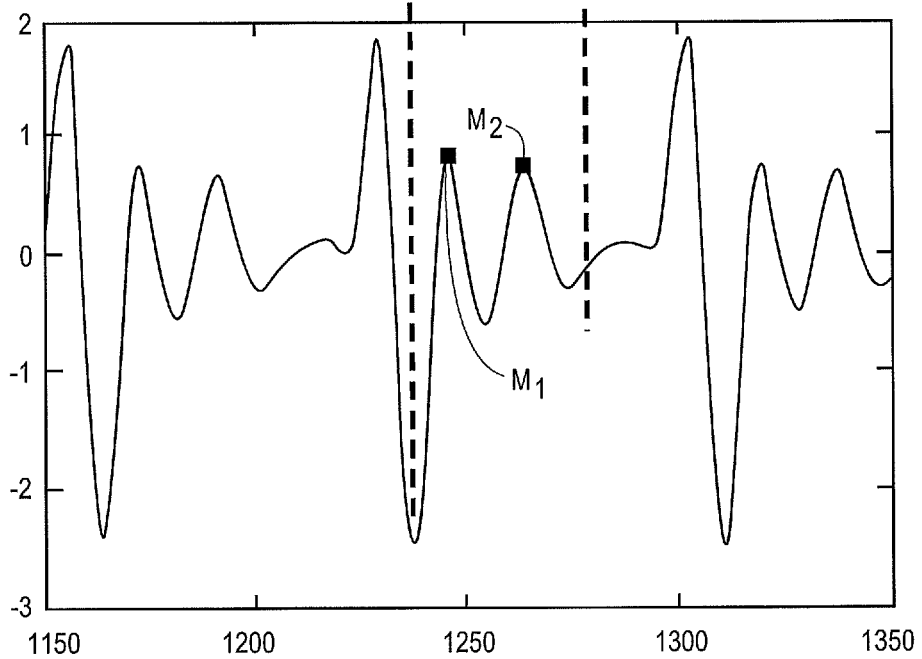

To further illustrate this method, FIG. 10 shows cardiac output data analyzed using this method. Specifically, FIG. 10A shows a waveform with about three heart beat cycles (and two local minima that could be the dichrotic notch) and FIG. 10B shows the first derivative function of the waveform shown in FIG. 10A. Point 10 of FIG. 10A is the start of the heart beat cycle being analyzed and dashed line 20 between FIGS. 10A and 10B shows the starting time point for the analysis of the first derivative function. Dashed line 30 indicates the search time point which is two-thirds the time interval between the starting point and the ending point 40, thus the period between dashed line 20 and dashed line 50 indicates the search window for finding local maximums in the first derivative function. Two local minimums $M_1$ and $M_2$ are found in the search window. Because more than one local maximum was found, the dichrotic notch is assigned to the second local minimum $M_2$, which corresponds to point 60 in FIG. 10A.

Figure 11:
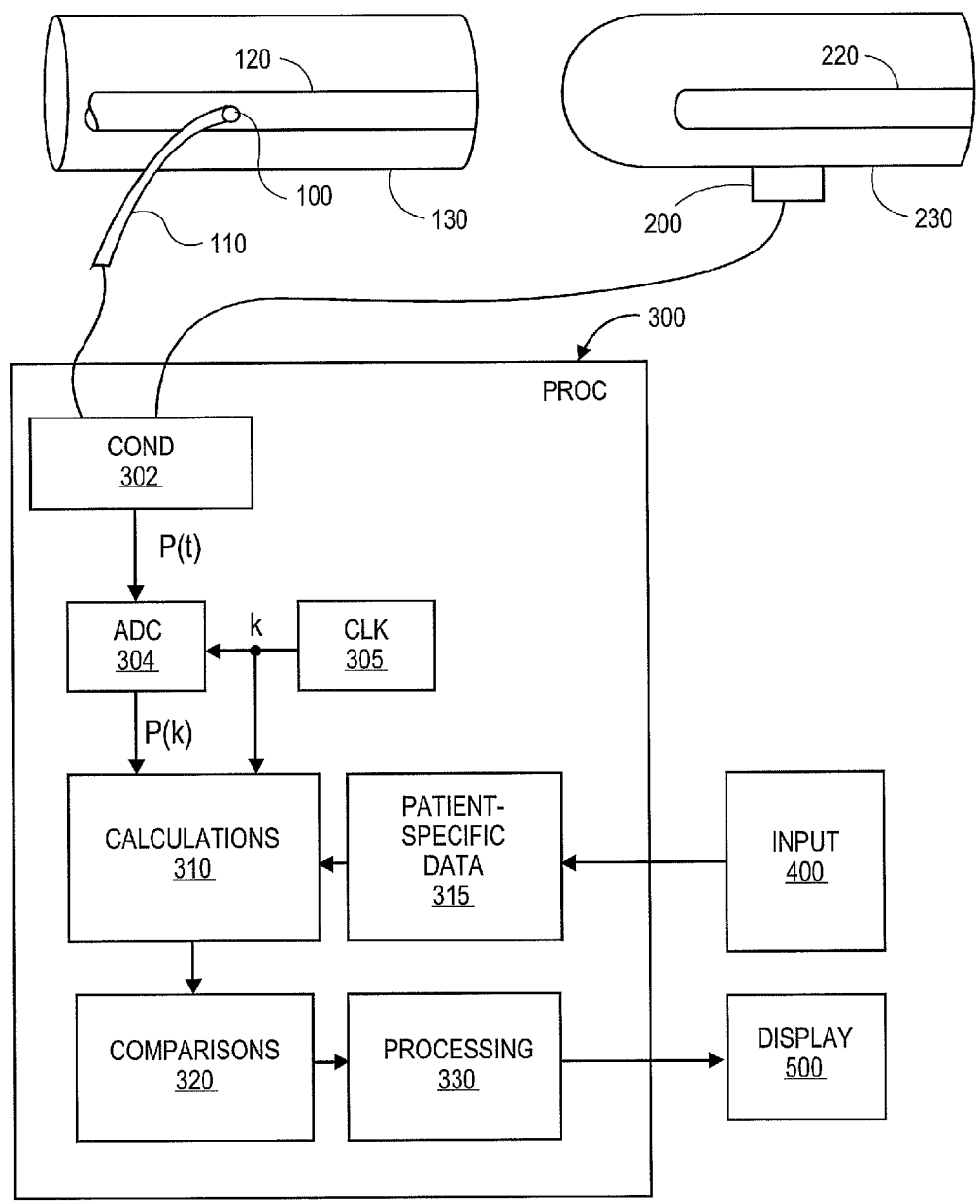
FIG. 11 is a block diagram showing the main components of a system to implement the methods described herein.

FIG. 11 shows the main components of a system that can be used to implement the methods described herein for detecting individual heart beat cycles in a cardiac output related waveform, detecting an error in an assigned starting point for an individual heart beat cycle in a cardiac output related waveform, detecting a dichrotic notch for an individual heart beat cycle in a cardiac output related waveform, and detecting an error in an assigned dichrotic notch for an individual heart beat cycle in a cardiac output related waveform. The methods may be implemented within an existing patient-monitoring device, or it may be implemented as a dedicated monitor. As is mentioned above, a cardiac output related waveform, or some other input signal proportional to, derived from, or a function of cardiac output, may be sensed in either or, indeed, both, of two ways: invasively and non-invasively. For convenience, the system is described as measuring arterial blood.

FIG. 11 shows both types of pressure sensing for the sake of completeness. In most practical applications of the methods described herein, either one or several variations will typically be implemented. In invasive applications of the methods described herein, a conventional pressure sensor 100 is mounted on a catheter 110, which is inserted in an artery 120 of a portion 130 of the body of a human or animal patient. The artery 120 is any artery in the arterial system, such as, for example, the femoral, radial or brachial artery. In the non-invasive applications of the methods described herein, a conventional pressure sensor 200, such as a photo-plethysmographic blood pressure probe, is mounted externally in any conventional manner, for example using a cuff around a finger 230 or a transducer mounted on the wrist of the patient. FIG. 11 schematically shows both types.

The signals from the sensors 100, 200 are passed via any known connectors as inputs to a processing system 300, which includes one or more processors and other supporting hardware and system software (not shown) usually included to process signals and execute code. The methods described herein may be implemented using a modified, standard, personal computer, or may be incorporated into a larger, specialized monitoring system. For use with the methods described herein, the processing system 300 also may include, or is connected to, conditioning circuitry 302 which performs normal signal processing tasks such as amplification, filtering, or ranging, as needed. The conditioned, sensed input pressure signal P(t) is then converted to digital form by a conventional analog-to-digital converter ADC 304, which has or takes its time reference from a clock circuit 305. As is well understood, the sampling frequency of the ADC 304 should be chosen with regard to the Nyquist criterion so as to avoid aliasing of the pressure signal (this procedure is very well known in the art of digital signal processing). The output from the ADC 304 will be the discrete pressure signal P(k), whose values may be stored in conventional memory circuitry (not shown).

The values P(k) are passed to or accessed from memory by a software module 310 comprising computer-executable code for implementing one or more aspects of the methods as described herein. The design of such a software module 310 will be straight forward to one of skill in the art of computer programming. Additional comparisons and/or processing as used by a method can be performed in additional modules such as 320 and 330.

If used, signal-specific data such as a previously determined dichrotic notch time point, a previously determined starting time point, and a previously determined end time point can be stored in a memory region 315, which may also store other predetermined parameters as needed. These values may be entered using any known input device 400 in the conventional manner.

As illustrated by FIG. 11, the results may be ultimately displayed on a conventional display or recording device 500 for presentation to and interpretation by a user. As with the input device 400, the display 500 will typically be the same as is used by the processing system for other purposes.

Exemplary embodiments of the present invention have been described above with reference to block diagrams and flowchart illustrations of methods, apparatuses, and computer program products. One of skill will understand that each block of the block diagrams and flowchart illustrations, and combinations of blocks in the block diagrams and flowchart illustrations, respectively, can be implemented by various means including computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

The methods described herein further relate to computer program instructions that may be stored in a computer-readable memory that can direct a computer or other programmable data processing apparatus, such as in a processor or processing system (shown as 300 in FIG. 11), to function in a particular manner, such that the instructions stored in the computer-readable memory produce an article of manufacture including computer-readable instructions for implementing the function specified in the blocks illustrated in FIG. 11. The computer program instructions may also be loaded onto a computer, the processing system 300, or other programmable data processing apparatus to cause a series of operational steps to be performed on the computer, the processing system 300, or other programmable apparatus to produce a computer-implemented process such that the instructions that execute on the computer or other programmable apparatus provide steps for implementing the functions specified in the blocks. Moreover, various software modules 310, 320, and 330 can be used to perform the various calculations and perform related method steps described herein also can be stored as computer-executable instructions on a computer-readable medium in order to allow the methods to be loaded into and executed by different processing systems.

Accordingly, blocks of the block diagrams and flowchart illustrations support combinations of means for performing the specified functions, combinations of steps for performing the specified functions, and program instruction means for performing the specified functions. One of skill will understand that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

The present invention is not limited in scope by the embodiments disclosed herein which are intended as illustrations of a few aspects of the invention and any embodiments which are functionally equivalent are within the scope of this invention. Various modifications of the methods in addition to those shown and described herein will become apparent to those skilled in the art and are intended to fall within the scope of the appended claims. Further, while only certain representative combinations of the method steps disclosed herein are specifically discussed in the embodiments above, other combinations of the method steps will become apparent to those skilled in the art and also are intended to fall within the scope of the appended claims. Thus a combination of steps may be explicitly mentioned herein; however, other combinations of steps are included, even though not explicitly stated. The term "comprising" and variations thereof as used herein is used synonymously with the term "including" and variations thereof and are open, non-limiting terms.

What is claimed is:

1. A method for detecting individual heart beat cycles in a cardiac output related waveform comprising:
    providing cardiac output related waveform data to a processing system;
    using the processing system to calculate a first derivative function for the waveform data and to reverse the time order of the data;
    using the processing system to determine the maximum amplitude in the first derivative function;
    using the processing system to compare the amplitude of the first derivative function to a threshold value, the threshold value being a percentage of the maximum amplitude in the first derivative function; and
    determining the start of a heart beat cycle by using the processing system to identify the first time the first derivative function equals zero immediately after the point at which the amplitude of the first derivative function is greater than the threshold value in the reversed time order data,
    wherein the first time the first derivative function equals zero indicates the beginning of a heart beat cycle.

2. The method of claim 1, wherein the threshold value is 75% of the maximum amplitude of the first derivative function.

3. The method of claim 1, wherein the threshold value is 60% of the maximum amplitude of the first derivative function.

4. The method of claim 1, wherein the threshold value is 30% of the maximum amplitude of the first derivative function.

5. The method of claim 1, further comprising verifying the number of heart beat cycles detected by additionally determining the start of each heart beat cycle by identifying each zero crossing in the first derivative function that occurs immediately prior in time to each point at which the amplitude of the first derivative function is greater than a lower threshold value; and
    comparing the number of heart beat cycles determined using the threshold value with the number of heart beats determined using the lower threshold value,
    wherein if the ratio of the number of heart beat cycles using the threshold value to the number of heart beat cycles using the lower threshold value is less than 65% and the number of beats per minute above 150 is greater than 35% of the beats per minute detected then using the heart beat cycles determined using the threshold value as the actual number of heart beat cycles, otherwise using the heart beat cycles determined using the lower threshold value as the actual number of heart beat cycles.

6. The method of claim 5, wherein the threshold value is 0.6 and the lower threshold value is 0.3.

7. The method of claim 5, wherein the threshold value is 0.75 and the lower threshold value is 0.6.

* * * * *